United States Patent [19]
Bellina

[11] 3,944,670
[45] Mar. 16, 1976

[54] PESTICIDAL DITHIAZOLIUM SALTS
[75] Inventor: Russell F. Bellina, Wilmington, Del.
[73] Assignee: E. I. Du Pont de Nemours and Company, Wilmington, Del.
[22] Filed: May 8, 1973
[21] Appl. No.: 358,395

Related U.S. Application Data
[63] Continuation-in-part of Ser. No. 304,793, Nov. 8, 1972, abandoned.

[52] U.S. Cl....... 424/250; 260/268 H; 260/306.8 R; 424/248; 424/270
[51] Int. Cl.²........................................... A01N 9/22
[58] Field of Search ...... 424/250; 260/268 H, 306.8

[56] References Cited
UNITED STATES PATENTS
3,166,564  1/1965  Diveley............................ 260/306.8
3,636,222  1/1972  Bader et al. ....................... 424/267

OTHER PUBLICATIONS
Chang et al., J. Econ. Ent. 65, 390 (1972).
Oliver et al., J. Med. Chem. 15, 315 (1972).
Oliver et al., J. Heter Chem., 9, 447 (1972).

Primary Examiner—Stanley J. Friedman
Assistant Examiner—Allen J. Robinson

[57] ABSTRACT

Dithiazolium salts of one of the following formulas:

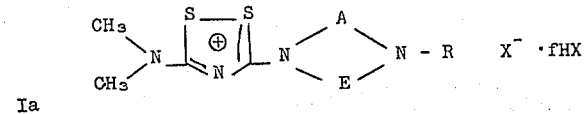

Ia

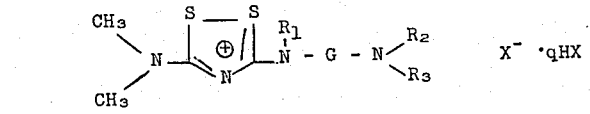

Ib where
R, $R_1$, $R_2$, and $R_3$ are certain organic radicals, the ring

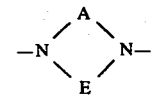

contains 5–8 atoms, and
A, E, and G are alkylene,
and their use as pesticides.

An exemplary compound: Hydrochloric acid salt of 3-dimethylamino-5-(4-methylpiperazin-1-yl)-1,2,4-dithiazolium chloride.

13 Claims, No Drawings

PESTICIDAL DITHIAZOLIUM SALTS

CROSS-REFERENCE TO RELATED APPLICATIONS

This application is a continuation-in-part of U.S. patent application Ser. No. 304,793 filed Nov. 8, 1972, now abandoned.

BACKGROUND OF THE INVENTION

U.S. Pat. No. 3,166,564 issued Jan. 19, 1965, discloses 3,5-bis(substituted amino)-1,2,4-dithiazolium salts of the formula

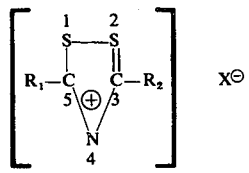

wherein

X represents an anion of an acid having an ionization constant of at least $1 \times 10^{-7}$, and $R_1$ and $R_2$ represent certain substituted secondary amino groups. Examples given for $R_1$ and $R_2$ include dimethylamino, diethylamino, dipropylamino, dibutylamino, dilaurylamino, didodecylamino, dicyclohexylamino, methylstearylamino, distearylamino, diphenylamino, ditolylamino, tolylphenylamino, dinaphthylamino, methylphenylamino, butyltolylamino, cyclohexylphenylamino, piperidino and morpholino. The compounds are said to be useful to defoliate plants, specifically cotton.

Some of the compounds disclosed in U.S. Pat. No. 3,166,564 are also known in the art as housefly chemosterilants [*J. Econ. Ent.* 62, 522 (1969), *J. Med. Chem.* 15, 315, (1972), and *J. Econ. Ent.* 65, 390 (1972)] and one of them, 3,5-bis(diethylamino)-1,2,4-dithiazolium chloride, is known as a Japanese beetle chemo-sterilant [*J. Econ. Ent.* 63, 458 (1970)].

It has also been discovered that compounds of U.S. Pat. No. 3,166,564 are miticides, insecticides, and fungicides. U.S. application Ser. No. 298,485, filed Oct. 18, 1972, now abandoned, as a continuation-in-part of U.S. application Ser. No. 149,328, filed June 2, 1971, now abandoned discloses the use of the compounds as miticides and insecticides. U.S. application Ser. No. 298,486, filed Oct. 18, 1972, now abandoned, discloses the use of the compounds as fungicides.

SUMMARY OF THE INVENTION

This invention is a class novel insecticidal, miticidal, and fungicidal dithiazolium salts which can be represented by the formula I*a*:

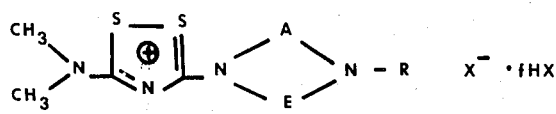

where $$A \text{ is } -(CH_2)_a- \text{ or } -(CH_2)_b-\overset{CH_3}{\underset{|}{CH}}-;$$

$a$ is 0 through 4;
$b$ is 1 or 2;

$$E \text{ is } -(CH_2)_d- \text{ or } -(CH_2)_e-\overset{CH_3}{\underset{|}{CH}}-;$$

$d$ is 2 through 5;
$e$ is 1 or 2;

with the provision that the total number of atoms in the ring

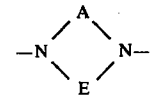

is between 5 and 8, inclusive;

R is alkyl of 1 through 6 carbon atoms;

with the provision that the sum of carbon atoms in A, E, and R is not more than 10;

$X^-$ is an anion of the corresponding acid HX having an ionization constant of at least $1 \times 10^{-7}$; and $f$ is 0 or 1;

and dithiazolium salts which can be represented by the formula I*b*:

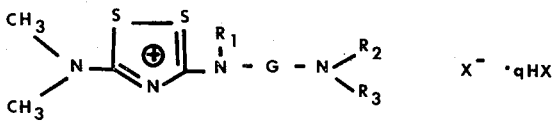

where $$G \text{ is } -(CH_2)_m- \text{ or } -(CH_2)_n-\overset{CH_3}{\underset{|}{CH}}-;$$

$m$ is 0 through 6;
$n$ is 1 or 2;
$R_1$ is methyl, $-(CH_2)_2-NR_2R_3$ or $-(CH_2)_3-NR_2R_3$;
$R_2$ is methyl or ethyl;
$R_3$ is alkyl of 1 through 6 carbon atoms; and
$R_2$ and $R_3$ taken together can be $-(CH_2)_p-$;
$p$ is 4 through 6;
with the provision that the sum of carbon atoms in G, $R_1$, $R_2$, and $R_3$ is not more than 10;
$X^-$ is an anion of the corresponding acid HX having an ionization constant of at least $1 \times 10^{-7}$; and
$q$ is 0, 1, or 2.

This invention also includes miticidal, fungicidal, and plant protective compositions containing the above compounds as active ingredient and methods for protecting plants from mites, fungi, aphids, Colorado potato bettle, Mexican bean beetle, and boll weevils by applying to the plant foliage a miticidally effective, fungicidally effective, or plant protective amount, but less than a defoliating amount, of at least one compound of formula I*a* or formula I*b*.

What is meant by a plant protective amount is that amount of at least one compound of formulas I*a* or I*b* that is necessary to prevents insects from causing damage to the plant. More specifically, under given conditions, a given species of insect can be killed with a certain quantity of a given compound or a given quantity of a combination of compounds of formula I*a* and formula I*b*. Under certain circumstances, a lesser quantity will be sufficient to protect the plant, i.e., even though the insect may not be killed, tests have shown that compounds of the present invention inhibit feeding of the insect or repel the insect. Thus, a plant protective amount includes not only an insecticidally effective amount, but also a lesser amount that is sufficient to prevent the insect from causing significant damage to the plant, by inhibiting the feeding of the insect, repelling the insect or otherwise. Similarly, a plant protective composition includes not only insecticidal composition, but also compositions which are not capable of killing the insect, but are capable of preventing the insect from causing significant damage by inhibiting the feeding of the insect, by repelling the insect, or otherwise.

In another embodiment this invention is a method for controlling mosquitoes, which comprises applying to the locus of mosquito larvae an insecticidally effective amount of at least one compound of either formula I*a* or formula I*b*.

In formulas I*a* and I*b*, $X^-$ is an anion of any acid HX with an ionization constant of at least $1 \times 10^{-7}$. Examples of such acids are HCl, HBr, HF, HI, $H_2SO_4$, HSCN, $H_3PO_4$, $H_2SO_3$, acetic acid, oxalic acid, tartaric acid, benzoic acid, and N-lauryl-N-methyl-2-aminoethanesulfonic acid. The miticidal, fungicidal, and plant protective activity of the salts of formulas I*a* and I*b* is attributable to the cation.

An advantage of the compounds of formulas I*a* and I*b* over those disclosed in U.S. Pat. No. 3,166,564 is that they are generally less phytotoxic.

DETAILED DESCRIPTION OF THE INVENTION

Preferred Compounds

Certain of the compounds of formulas I*a* and I*b* are preferred because of their higher activity. These include those compounds of formula I*a* where:
  A and E are $-(CH_2)_2-$; and
  R is alkyl of 1 through 4 carbon atoms; and those compounds of formula I*b* where:
  G is $-(CH_2)_2-$ or $-(CH_2)_3-$;
  $R_1$ is methyl;
  $R_2$ is methyl or ethyl; and
  $R_3$ is methyl or ethyl.

Most preferred because of their highest activity are the following compounds:
hydrochloric acid salt of 3-dimethylamino-5-(4-methylpiperazin-1-yl)-1,2,4-dithiazolium chloride
hydrobromic acid salt of 3-dimethylamino-5-(4-propylpiperazin-1-yl)-1,2,4-dithiazolium bromide
hydrobromic acid salt of 3-dimethylamino-5-[N-(2-dimethylaminoethyl)-N-methylamino]-1,2,4-dithiazolium bromide
hydrobromic acid salt of 3-dimethylamino-5-[N-(3-dimethylaminopropyl)-N-methylamino]-1,2,4-dithiazolium bromide

Synthesis of the Final Products

The compounds of formulas I*a* and I*b* can be made by oxidation of an appropriate dithiobiuret of formulas II*a* and II*b* in the presence of an acid HX.

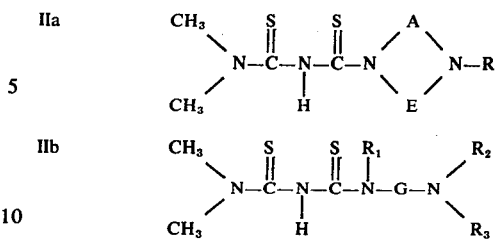

The reaction can be carried out under general conditions described in U.S. Pat. No. 3,166,564 for oxidation of dithiobiurets in the presence of an acid to produce dithiazolium salts. To make the compounds where $f$ or $q$ is 1 an additional equivalent of acid is used to form the desired salt. To make the compounds where $q$ is 2, two additional equivalents of acid are used. As taught by the same reference, one salt can be converted to a salt of another acid by a simple displacement or by reacting one salt with a metal salt of another acid.

Synthesis of the Precursor Dithiobiurets

The dithiobiurets of formulas II*a* and II*b* and their use as insecticides, fungicides, and miticides are the subject matter of two copending U.S. pat. applications, Ser. Nos. 358,394, filed May 8, 1973 now U.S. Pat. No. 3,890,322 issued June 17, 1975 and 358,396, filed May 8, 1973, now abandoned, filed simultaneously herewith by Russell F. Bellina and Colin L. McIntosh, respectively. These precursor dithiobiurets can be prepared by the general procedure described in the above-mentioned U.S. Pat. No. 3,166,564 and further described in *J. Med. Chem.*, 14, 772 (1971) i.e., by reacting an appropriate substituted thiocarbamoyl chloride with an alkali metal or ammonium thiocyanate to form a corresponding substituted thiocarbamoyl isothiocyanate, and then reacting the latter with an appropriate secondary amine.

The following Examples are given to illustrate the above processes. All parts are by weight unless specified otherwise.

EXAMPLE 1

Preparation of the hydrobromic acid salt of 3-dimethylamino-5-(4-methylpiperazin-1-yl)-1,2,4-dithiazolium bromide To a solution of 14.6 parts of dimethylthiocarbamoyl isothiocyanate in 100 parts of acetone at room temperature was added dropwise over a 15-minute period 10 parts of N-methylpiperazine. To the resulting mixture was added dropwise 34 parts of 48% aqueous hydrobromic acid over 15 minutes followed by the addition of 11.35 parts of 30% hydrogen peroxide over a 30-minute period. The temperature of all of the previous reactions was maintained at 25°–35°C. The reaction was then evaporated under reduced pressure at 50°C. to afford the crude product as an oil. Trituration with acetone induced crystallization. The crude solid was recrystallized from ethanol to afford 25 parts of product, m.p. 244°–246° C. dec. The analytical sample was recrystallized from ethanol/water to furnish the desired product, m.p. 256°–257° C. dec.

EXAMPLE 2

Preparation of the hydrochloric acid salt of 3-dimethylamino-5-(4-methylpiperazin-1-yl)-1,2,4-dithiazolium chloride A solution of 100 parts of N-methylpiperazine in 100 parts of acetone was added dropwise to a solution of 142 parts of dimethylthiocarbamoyl isothiocyanate in 650 parts of acetone at 10° to 15° C. This solution was allowed to warm to room temperature and stirred for 16 hours, during which time the solid dithiobiuret intermediate precipitated. The solid was filtered, washed with acetone, and air dried to furnish 120 parts of the required dithiobiuret, m.p. 160° C. 47 Parts of liquified chlorine was then added dropwise to a solution of 110 parts of the above dithiobiuret in 300 parts of dimethylformamide at 20° to 30° C. This mixture was allowed to react at room temperature for 2 hours, during which time a precipitate formed. The reaction mixture was filtered to afford 145 parts of crude product, m.p. 188° – 191° C. Recrystallization from ethanol provided 60 parts of the pure, yellow hydrochloric acid salt of 3-dimethylamino-5-(4methylpiperazine-1-yl)-1,2,4-dithiazolium chloride, m.p. 223° – 226° C.

EXAMPLE 3

Preparation of the hydrobromic acid salt of 3-dimethylamino-5-(4-propylpiperazin-1-yl)-1,2,4-dithiazolium bromide 12 Parts of N-propylpiperazin in 50 parts of acetone was added dropwise to a solution of 14.2 parts of dimethylthiocarbamoyl isothiocyanate in 100 parts of acetone at 10°–15° C. The solution was allowed to warm to room temperature, stirred for 2 hours, filtered, and evaporated under reduced pressure to remove the acetone therefrom. The resulting crude dithiobiuret intermediate was added to 50 parts of a 10% sodium hydroxide solution. The resulting solution was washed twice with 50 parts of chloroform and neutralized with glacial acetic acid. The solution was then extracted twice with 50 parts of methylene chloride. The organic extracts were dried, filterd, and evaporated under reduced pressure to afford the intermediate dithiobiuret as a viscous oil. 5.8 Parts of the dithiobiuret product was dissolved in 30 parts of methanol at 10°–20° C. and bromine was added dropwise thereto until the orange color persisted. The solid which formed during the bromine addition was filtered to afford the crude product, a yellow solid, m.p. 215.5° C. Recrystallization from an ethanol-water mixture provided one part of the hydrobromic acid salt of 3-dimethylamino-5-(4-propyl-piperazin-1-yl)-1,2,4-dithiazolium bromide, m.p. 264° C.

EXAMPLE 4

Preparation of the hydrobromic acid salt of 3-dimethylamino-5-[N-(3-dimethylaminopropyl)-N-methylamino]-1,2,4-dithiazolium bromide A solution of 5.8 parts of N,N,N'-trimethyltrimethylenediamine in 40 parts of acetone was added dropwise to a solution of 7.1 parts of dimethylthiocarbamoyl isothiocyanate in 40 parts of acetone at 10°–15° C. This mixture was allowed to warm to room temperature and was stirred for one hour. 16.5 Parts of 48% hydrobromic acid was then added to the reaction mixture. This mixture was then cooled to 10° C. and 6 parts of 30% hydrogen peroxide was added dropwise. This mixture was allowed to warm to room temperature, was stirred for 1 hour, and then evaporated under vacuum. The residue was then added to 200 parts of ethanol, concentrated slowly to about 100 parts, filtered, and then fully evaporated to afford 8 parts of the desired hydrobromic acid salt of 3-dimethylamino-5-[N-(3-dimethylaminopropyl)-N-methylamino]-1,2,4-dithiazolium bromide as a viscous oil.

EXAMPLE 5

Preparation of the hydrobromic acid salt of 3-dimethylamino-5-[N-(2-dimethylaminoethyl)-N-methylamino]-1,2,4-dithiazolium bromide A solution of 10.2 parts of N,N,N'-trimethylethylenediamine in 20 parts of acetone was added dropwise to a solution of 14.2 parts of dimethylthiocarbamoyl isothiocyanate in 100 parts of acetone at 10°–15° C. The resulting solution was allowed to warm to room temperature and stirred for 2 hours. This solution was then filtered and evaporated under reduced pressure. The residue was added to 50 parts of a 10% sodium hydroxide solution. This solution was washed with 100 parts of chloroform, neutralized with glacial acetic acid, and then extracted twice with 50 parts of methylene chloride. The combined methylene chloride extracts were dried, filtered, and evaporated under reduced pressure to give 13 parts of the crude dithiobiuret product. This product was then recrystallized from ethanol to afford 5 parts of the required dithiobiuret, m.p. 93°–94° C. 5 Parts of this dithiobiuret were dissolved in 30 parts of methanol at 10° C. Bromine was added dropwise to this solution until the orange color persisted. The reaction mixture was stirred at room temperature for one hour and was then filtered to give 8 parts of the crude product, m.p. 140° C. This product was recrystallized from ethanol to provide 3 parts of the hydrobromic acid salt of 3-dimethylamino-5-[N-(2-diethylaminoethyl)-N-methylamino]-1,2,4-dithiazolium bromide, m.p. 244° C.

By using an appropriate amine with an appropriate acid or an appropriate halogen, the following compounds can be prepared similarly:

thiocyanic acid salt of 3-dimethylamino-5-(1,2,2-trimethylhydrazino)-1,2,4-dithiazolium thiocyanate N-lauryl-N-methyl-2-aminoethane sulfonic acid salt of 3-dimethylamino-5-(1,2,2-trimethylhydrazino)-1,2,4-dithiazolium N-lauryl-N-methyl-2-aminoethane sulfonate hydrobromic acid salt of 3-dimethylamino-5-(1-methyl-2-ethyl-2-hexylhydrazino)-1,2,4-dithiazolium bromide hydrobromic acid salt of 3-dimethylamino-5-[N-(azacyclohept-1-yl)-N-methylamino]-1,2,4-dithiazolium bromide hydrochloric acid salt of 3-dimethylamino-5-[N-pyrrolidin-1-yl)-N-methylamino]-1,2,4-dithiazolium chloride hydroiodic acid salt of 3-dimethylamino-5-[1-(2-dimethylaminoethyl)-2,2-diethylhydrazino]-1,2,4-dithiazolium iodide hydrobromic acid salt of 3-dimethylamino-5-[1-(3-diethylaminopropyl)-2,2-dimethylhydrazino]-1,2,4-dithiazolium bromide hydrobromic acid salt of 3-dimethylamino-5-[N-(pyrrolidin-1-yl)-N-(2-dimethylaminoethyl)amino]-1,2,4-dithiazolium bromide hydrochloric acid salt of 3-dimethylamino-5-{N-(pyrrolidin-1-yl)-N-[2-(N-pyrrolidin-1-yl)ethyl]-amino}-1,2,4-dithiazolium chloride
acetic acid salt of 3-dimethylamino-5-[N,N-bis(2-dimethylaminoethyl)amino]-1,2,4-dithiazolium acetate
hydrochloric acid salt of 3-dimethylamino-5-[N-(6-dimethylaminohexyl)-N-methylamino]-1,2,4-dithiazolium chloride
oxalic acid salt of 3-dimethylamino-5-[1-(2diethylaminoethyl)-N-methylamino]-1,2,4-dithiazolium oxalate
hydrochloric acid salt of 3-dimethylamino-5-[N,N-bis-(2-diethylaminoethyl)amino]-1,2,4-dithiazolium chloride
hydrochloric acid salt of 3-dimethylamino-5-{N-[2-(pyrrolidin-1-yl)ethyl]-N-methylamino}-1,2,4-dithiazolium chloride
hydrochloric acid salt of 3-dimethylamino-5-{N-[2-(piperadin-1-yl)ethyl]-N-methylamino}-1,2,4-dithiazolium chloride
hydrobromic acid salt of 3-dimethylamino-5-{N-[5-(pyrrolidin-1-yl)pentyl]-N-methylamino}-1,2,4-dithiazolium bromide
hydrobromic acid salt of 3-dimethylamino-5-{N-[3-(N-ethyl-N-butylamino)propyl]-N-methylamino}-1,2,4-dithiazolium bromide
hydroiodic acid salt of 3-dimethylamino-5-(5-methyl-1,5-diazacycloct-1-yl)-1,2,4-dithiazolium iodide
hydroiodic acid salt of 3-dimethylamino-5-(4-ethyl-1,4-diazacycloct-1-yl)-1,2,4-dithiazolium iodide
hydrochloric acid salt of 3-dimethylamino-5-(4,5,6-trimethyl-1,5-diazacycloct-1-yl)-1,2,4-dithiazolium chloride
hydrochloric acid salt of 3-dimethylamino-5-(2,8-dimethyl-5-ethyl-1,5-diazacycloct-1-yl)-1,2,4-dithiazolium chloride
hydrobromic acid salt of 3-dimethylamino-5-(4,5,8-trimethyl-1,5-diazacycloct-1-yl)-1,2,4-dithiazolium bromide
hydrobromic acid salt of 3-dimethylamino-5-(4-methyl-1,4-diazacyclohept-1-yl)-1,2,4-dithiazolium bromide
hydrobromic acid salt of 3-dimethylamino-5-(4-pentyl-1,4-diazacyclohept-1-yl)-1,2,4-dithiazolium bromide
hydrochloric acid salt of 3-dimethylamino-5-(2-methyl-1,2-diazacyclohept-1-yl)-1,2,4-dithiazolium chloride
hydrochloric acid salt of 3-dimethylamino-5-(2propyl-1,2-diazacyclopent-1-yl)-1,2,4-dithiazolium chloride
hydrochloric acid salt of 3-dimethylamino-5-(2-hexyl-1,2-diazacyclohex-1-yl)-1,2,4-dithiazolium chloride
hydroiodic acid salt of 3-dimethylamino-5-(2,3-dimethyl-1,2-diazacyclopent-1-yl)-1,2,4-dithiazolium iodide
hydroiodic acid salt of 3-dimethylamino-5-(2-hexyl-2-methyl-1,2-diazacyclopent-1-yl)-1,2,4-dithiazolium iodide
sulphuric acid salt of 3-dimethylamino-5-(2,5-dimethyl-1,2-diazacyclopent-1-yl)-1,2,4-dithiazolium bisulfate
sulfuric acid salt of 3-dimethylamino-5-(3,4,5-trimethylpiperazin-1-yl)-1,2,4-dithiazolium bisulfate
benzoic acid salt of 3-dimethylamino-5-(2,4,6-trimethylpiperazin-1-yl)-1,2,4-dithiazolium benzoate
acetic acid salt of 3-dimethylamino-5-(2,4,5-trimethylpiperazin-1-yl)-1,2,4-dithiazolium acetate
hydrochloric acid salt of 3-dimethylamino-5-(2,6-dimethyl-4-isopropylpiperazin-1-yl)-1,2,4-dithiazolium chloride
hydrofluoric acid salt of 3-dimethylamino-5-(3-methyl-1,3-diazacyclopent-1-yl)-1,2,4-dithiazolium fluoride
hydrofluoric acid salt of 3-dimethylamino-5-(3-pentyl-1,3-diazacyclopent-1-yl)-1,2,4-dithiazolium fluoride
hydrobromic acid salt of 3-dimethylamino-5-(4-isopropylpiperazin-1-yl)-1,2,4-dithiazolium bromide
hydrobromic acid salt of 3-dimethylamino-5-(4-sec-butylpiperazin-1-yl)-1,2,4-dithiazolium bromide
oxalic acid salt of 3-dimethylamino-5-(4-ethylpiperazin-1-yl)-1,2,4-dithiazolium oxalate
hydroiodic acid salt of 3-dimethylamino-5-[N-2-dimethylamino-1-methylethyl)-N-methylamino]-1,2,4-dithiazolium iodide
hydroiodic acid salt of 3-dimethylamino-5-[N-(2-dimethylamino-2-methylethyl)-N-methylamino]-1,2,4-dithiazolium iodide
hydrochloric acid salt of 3-dimethylamino-5-[N-(3-dimethylamino-1-methylpropyl)-N-methylamino]-1,2,4-dithiazolium chloride
hydrochloric acid salt of 3-dimethylamino-5-[N-(3-dimethylamino-3-methylpropyl)-N-methylamino]-1,2,4-dithiazolium chloride
hydroiodic acid salt of 3-dimethylamino-5-{N-[(2-pyrrolidin-1-yl)-1-methylethyl]-N-methylamino}-1,2,4-dithiazolium iodide
hydroiodic acid salt of 3-dimethylamino-5-{N-[3-(azacyclohept-1-yl)-1-methylpropyl]-N-methylamino}-1,2,4-dithiazolium iodide

EXAMPLE 6

Preparation of
3-dimethylamino-5-(4-methylpiperazin-1-yl)-1,2,4-dithiazolium bromide A solution of 0.54 parts of sodium methoxide in 10 parts of ethanol was added dropwise to a slurry of 4 parts of the hydrobromic acid salt of 3-dimethylamino-5-(4-methylpiperazin-1-yl)-1,2,4-dithiazolium bromide (prepared as in Example 1 above) in 40 parts of ethanol at 10° C. This mixture was allowed to warm to room temperature and was stirred for 5 days. The resulting solution was then filtered and evaporated under reduced pressure. The residue was extracted with acetonitrile, filtered, and evaporated to furnish 2.4 parts of a viscous clear yellow oil. The oil was induced to crystallize by trituration with acetone. The product (1.4 parts) was filtered, washed with acetone, then washed with hexane, and air dried. The acetone filtered and washings were combined and a second crop of 0.6 parts of the product was filtered therefrom. Infrared analysis of the second crop indicated it contained less hydrobromic acid than the first crop. The second crop was recrystallized from an acetone hexane mixture, m.p. 103°–105° C.

Calculated 24.6% Br.
Found 23.8% Br.

EXAMPLE 7

Preparation of
3-dimethylamino-5-(4-methylpiperazin-1-yl)-1,2,4-dithiazolium chloride 13.4 Parts of concentrated hydrochloric acid was added dropwise to a mixture of 24.6 parts of the dithiobiuret intermediate of Example 1 in 100 parts of acetone at 10° to 20° C. This was followed by the dropwise addition of 11.4 parts of 30% hydrogen peroxide. The reaction mixture was then stirred for 1 hour, during which time a yellow oil precipitated. 100 Parts of water was added to this mixture. The resulting aqueous solution was washed three times with 50 part portions of chloroform and then evaporated under reduced pressure to afford the 3-dimethylamino-5-(4-methylpiperazin-1-yl)-1,2,4-dithiazolium chloride product as a hydroscopic solid.

The following compounds can be prepared similarly by using an appropriate acid salt in the method described in Example 6 or by using an appropriate amine and an appropriate acid in the method described in Example 7:

3-dimethylamino-5-(4-methyl-1,4-diazacyclohept-1-yl)-1,2,4-dithiazolium bromide
3-dimethylamino-5-(4-pentyl-1,4-diazacyclohept-1-yl)-1,2,4-dithiazolium bromide
3-dimethylamino-5-(2-methyl-1,2-diazacyclohept-1-yl)-1,2,4-dithiazolium chloride
3-dimethylamino-5-(2-propyl-1,2-diazacyclopent-1-yl)-1,2,4-dithiazolium fluoride
3-dimethylamino-5-(2-hexyl-1,2-diazacyclohex-1-yl)-1,2,4-dithiazolium iodide
3-dimethylamino-5-(2,3-dimethyl-1,2-diazacyclopent-1-yl)-1,2,4-dithiazolium iodide
3-dimethylamino-5-(2-hexyl-2-methyl-1,2-diazacyclopent-1-yl)-1,2,4-dithiazolium iodide
3-dimethylamino-5-(2,5-dimethyl-1,2-diazacyclopent-1-yl)-1,2,4-dithiazolium bisulfate
3-dimethylamino-5-(3,4,5-trimethylpiperazin-1-yl)-1,2,4-dithiazolium bisulfate
3-dimethylamino-5-(2,4,6-trimethylpiperazin-1-yl)-1,2,4-dithiazolium benzoate
3-dimethylamino-5-(2,4,5-trimethylpiperazine-1-yl)-1,2,4-dithiazolium acetate
3-dimethylamino-5-(2,6-dimethyl-4-isopropylpiperazin-1-yl)-1,2,4-dithiazolium chloride
3-dimethylamino-5-(3-methyl-1,3-diazacyclopent-1-yl)-1,2,4-dithiazolium fluoride
3-dimethylamino-5-(3-pentyl-1,3-diazacyclopent-1-yl)-1,2,4-dithiazolium fluoride
3-dimethylamino-5-(3-isopropylpiperazin-1-yl)-1,2,4-dithiazolium bromide
3-dimethylamino-5-(3-sec-butylpiperazin-1-yl)-1,2,4-dithiazolium bromide
3-dimethylamino-5-(3-ethylpiperazin-1-yl)-1,2,4-dithiazolium oxalate

EXAMPLE 8

Preparation of the dihydrobromic acid salt of 3-dimethylamino-[N,N-bis(2-dimethylaminoethyl)amino]-1,2,4-dithiazolium bromide 15.9 Parts of 1,1,7,7-tetramethyldiethylenetriamine is added dropwise over a 15-minute period to a solution of 14.6 parts of dimethylthiocarbamoyl isothiocycanate in 100 parts of acetone. 51 Parts of 48% hydrobromic acid is then added dropwise to the resulting mixture after which 11.35 parts of a 30% hydrogen peroxide solution at 15° to 20° C. is added to this mixture over a 30-minute period. The dihydrobromic acid salt product will separate from the reaction mixture and can be purified by usual procedures.

By using the appropriate amine and acid, the following compounds can be prepared similarly:

dihydrobromic acid salt of 3-dimethylamino-5-[1-(3-diethylaminopropyl)-2,2-dimethylhydrazino]-1,2,4-dithiazolium bromide
dihydroiodic acid salt of 3-dimethylamino-5-[N-(pyrrolidin-1-yl)-N-(2-dimethylaminoethyl)amino]-1,2,4-dithiazolium iodide
dihydrochloric acid salt of 3-dimethylamino-5-[N-(pyrrolidin-1-yl)-N-(2-pyrrolidin-1-yl)ethyl)amino]-1,2,4-dithiazolium chloride
diacetic acid salt of 3-dimethylamino-5-[N,N-bis(2-dimethylaminoethyl)amino]-1,2,4-dithiazolium acetate
dihydrochloric acid salt of 3-dimethylamino-5-[N,N-bis(2-dimethylaminoethyl)amino]-1,2,4-dithiazolium chloride Formulation of the Compounds Miticidal, fungicidal, and plant protective compositions can be prepared by mixing at least one compound of formulas Ia and Ib with an inert carrier and/or a surface-active agent to provide water-soluble powders, dusts, and liquid concentrates. The inert carrier can be a finely divided solid, water, or an organic liquid. The surface-active agent can by any anionic, cationic, or non-ionic agent which has heretofore been generally employed in pest-control compositions or an equivalent. Suitable surface-active agents are set forth, for example, in "Detergents and Emulsifiers 1970 Annual" by John W. McCutcheon, Inc.

Water-soluble powders of this invention contain at least one compound of formulas Ia and Ib together with an inert, solid carrier which may itself be either water-soluble or water-insoluble. One or more surface-active agents may also be present to improve speed of wetting, dispersion, and solution in water.

The most suitable water-insoluble carriers are synthetic silicas, magnesium silicate, and natural clays, such as, diatomaceous earth, kaolinites, attapulgite clay, and the like. Water-soluble carriers include sugar, calcium sulfite dihydrate, sodium sulfite, urea, and the like.

The water-soluble powder formulations contain from about 25 to 99% by weight of at least one compound of formulas Ia and Ib and 1 to 75% by weight of inert carrier. Preferably, they also contain about 0.1% to 10% by weight of surface-active agents replacing equivalent amounts of inert carrier.

The more dilute of these water-soluble powders can also be used as dusts, and more concentrated compositions can be diluted with conventional dust diluents, such as to a range of 1 to 25% active ingredient.

Liquid concentrates of the invention contain at least one compound of formulas Ia and Ib together with a solvent consisting of water or an organic liquid or any suitable mixture of these. Organic liquids which can be used include dimethylformamide, ethylene glycol, diethylene glycol, propylene glycol, the monomethyl or ethyl ethers of the preceding glycols, methanol, ethanol, propanol, acetone, and other ketones.

Liquid concentrates of the invention contain from about 10 to about 60% by weight of active ingredient (at least one compound of formulas Ia and Ib), with the remainder comprising the solvents listed above either individually or in admixture.

These liquid compositions can be diluted with water and applied in the conventional manner to plants, but they are also particularly suitable for application at high concentrations in the typical ultra-low-volume or or low-volume application from aircraft or ground sprayer. The water-soluble powders can also be dissolved or dispersed in appropriate liquid carriers and applied as low-volume sprays.

Compositions of this invention can contain in addition to at least one compound of formulas I$a$ and I$b$ conventional insecticides, miticides, bactericides, and fungicides, or other agricultural chemicals such as fruit sap agent, fruit thinning compounds, fertilizer ingredients, and the like.

The following examples illustrate suitable formulations of the compounds of the present invention. All percents are by weight.

EXAMPLE 9

| | Percent |
|---|---|
| Hydrobromic acid salt of 3-dimethylamino-5-[N-2-dimethylaminoethyl)-N-methylamino]-1,2,4-dithiazolium bromide | 25.0 |
| Water | 25.0 |
| Ethylene glycol | 40.0 |
| Ethanol | 10.0 |

The above ingredients are blended until a homogeneous solution results.

EXAMPLE 10

| | Percent |
|---|---|
| Hydrobromic acid salt of 3-dimethylamino-5-[N-(3-dimethylaminopropyl)-N-methylamino]-1,2,4-dithiazolium bromide | 35.0 |
| Dimethyl formamide | 65.0 |

The active compound is blended with the dimethyl formamide with a homogeneous solution results.

EXAMPLE 11

| | Percent |
|---|---|
| Hydrochloric acid salt of 3-dimethylamino-5-(4-methylpiperazin-1-yl)-1,2,4-dithiazolium chloride | 95.0 |
| Sodium dioctyl sulfosuccinate | 0.5 |
| Synthetic silica | 4.5 |

The above ingredients are blended, ground to pass an 0.50 mm screen and reblended.

EXAMPLE 12

| | Percent |
|---|---|
| Hydrobromic acid salt of 3-dimethyl-amino-5-(4-ethylpiperazin-1-yl)-1,2,4-dithiazolium bromide | 80.0 |
| Kaolinite clay | 18.5 |
| Sodium lignin sulfonate | 0.5 |
| Sodium alkylnaphthalene sulfonate | 1.0 |

The above ingredients are blended, micropulverized to pass an 0.149 mm screen and reblended.

EXAMPLE 13

| | Percent |
|---|---|
| Sulfuric acid salt of 3-dimethyl-amino-5-(4-methylpiperazin-1-yl)-1,2,4-dithiazolium bisulfate | 50.0 |
| Sucrose | 49.0 |
| Methylated cellulose | 0.5 |

EXAMPLE 13 -continued

| | Percent |
|---|---|
| Sodium dioctyl sulfosuccinate | 0.5 |

The above ingredients are blended, ground to pass an 0.30 mm screen and reblended.

Use of the Compounds

Many species of mites which cause damage to fruits, field crops, vegetables, ornamentals, animals, birds, and man are controlled by the compounds of this invention. The following is a list of representative susceptible mites along with the types of damage that they can cause: *Panonychus ulmi* (European red mite) and *Tetranychus urticae* (two spotted mite) which are commonly called "orchard mites," and which attach a great many deciduous trees, such as apple, pear, cherry, plum, and peach trees; *Tetranychus atlanticus* (Atlantic or strawberry mite), *T. cinnabarinus* (carmine spider mite) and *T. pacificus* (Pacific mite); which attach cotton and numerous other crop plants; *Paratetranychus citri* (citrus red mite) and others which attach citrus; *Phyllocoptruta oleivora* which causes citrus rust; *Bryobia praetiosa* (clover mite) which attacks clover, alfalfa, and other crops; *Aceria neocynodomis* which attacks grasses and other plants; *Tyrophagus lintneri* which is a serious pest in stored foods and on cultivated mushrooms; *Lepidoglyphus destructor* which injures Kentucky bluegrass seed in storage, and *Dermanyssus gallinae* (poultry mite) which reduce egg production and increase mortality of young chicks.

The compounds of formulas I$a$ and I$b$ are also useful for control of certain insect species such as: the apple aphid, *Aphis pomi;* bean aphid, *Aphis fabae;* green peach aphid, *Myzus persicae;* pea aphid, *Macrosiphum pisi;* potato aphid, *Macrosiphum euphobiae;* Colorado potato beetle, *Leptinotarsa decemlineata;* Mexican bean beetle, *Epilachna varivestis;* Southern armyworm, *Prodenia eridania;* bollworms, *Heliothis zea* and *Heliothis virescens;* mosquitoes, *Aedes* spp., *Anopheles* spp., and *Culex* spp.,; and boll weevils, *Anthonomus grandis.*

The compounds of formulas I$a$ and I$b$ are called fungicides, although in the strictest sense they do not necessarily kill fungi; they have an anti-sporulant effect or fungi, and control many plant diseases, including the tomoto late blight pathogen, *Phytophthora infestans,* the cucumber powdery mildew pathogen, *Erysiphe cichoracearum,* the apple scab pathogen, *Venturia inaequalis,* and the downy mildew pathogen, *Pseudoperonospora cubensis.*

The compounds of formulas I$a$ and I$b$ can be used for the protection of plants such as fruit-bearing trees, nut-bearing trees, ornamental trees, forest trees, vegetable crops, horticultural crops (including ornamental, small fruit and berries), and grain and seed crops. They are especially suited to protect apple, citrus, and peach trees, cotton, potatoes, peas, corn, and beans from mites, fungi, and certain insects.

Rates for application of the compounds of formulas I$a$ and I$b$ to field crops are from 0.01 to 4 kilograms of active ingredient per hectare. For the more active compounds, including the preferred compounds, rates in the range of 0.01 to 0.8 kg/ha. are preferred. The compounds should be applied to ornamental, nut, and fruit trees by spraying to run-off with a solution or suspension containing about 5 to 4,000 ppm, preferably about 10 to 2,000 ppm and most preferably about 40 to 500 ppm of active ingredient. The compounds, of course, vary in their pesticidal activity and phytotoxicity. The untreated control plants were badly damaged by the existing mites and large numbers of eggs were present.

The following table lists results of similar experiments with other compounds of the invention:

| Name | Concentration ppm | % Control | Phytotoxicity |
|---|---|---|---|
| hydrobromic acid salt of 3-dimethylamino-5-[N-(2-dimethylaminoethyl)-N-methylamino]-1,2,4-dithiazolium bromide | 10 | 100 | None |
| hydrobromic acid salt of 3-dimethylamino-5-[N-(3-dimethylaminopropyl)-N-methylamino]-1,2,4-dithiazolium bromide | 20 | 100 | None |
| hydrobromic acid salt of 3-dimethylamino-5-(4-N-propylpiperazinyl)-1,2,4-dithiazolium bromide | 500 | 100 | None | compounds must be used in an amount which is effective to control the pests but less than the amount which will cause defoliation or other severe symptoms of phytotoxicity. The optimum amount for a given compound depends upon a number of variables which are well known to those skilled in the art of plant protection. These include, but are not limited to, the species of mite, fungus, or insect to be controlled, weather conditions expected, type of crop, stage of development of the crop and the interval between applications.

It may be necessary or desirable to repeat application within the ranges given one or more times at intervals of 1 to 60 days.

The compounds of formulas Ia and Ib may be used for control of mosquito larvae breeding in swampy and other moist locations. The quantity of chemicals used depends on the amount of water present in the area and on the percent control of the larvae desired. Greater amounts of water present and a desired high percent kill require correspondingly greater amounts of active ingredient. In general, marshy areas where the water does not exceed one foot in depth may require 0.1 to 3 kg of active ingredient per hectare. The amount actually used should be predetermined from a knowledge of the area to be treated.

EXAMPLE 14

The foliage of two Red Kidney bean plants was infested with approximately 200 two-spotted mites (*Tetranychus urticae* (approximately 50 per leaf) and then sprayed to run-off with a solution containing 10 ppm of the hydrochloric acid salt of 3-dimethylamino-5-(4-methylpiperazin-1-yl)-1,2,4-dithiazolium chloride. No living mites could be found on these plants one week after treatment. Treated plants were growing vigorously and no phytotoxicity was observed. The leaves of

EXAMPLE 15

Foliar sprays of the hydrochloric acid salt of 3-dimethylamino-5-(4-methylpiperazin-1-yl)-1,2,4-dithiazolium chloride (I) protect foliage of cotton plants from attack by boll weevil for an extended period of time. The compound does not kill the weevils, but prevents or inhibits them from feeding. This experiment was based on excising treated leaves of uniform size and exposing them to weevils as indicated.

| Compound | Concentration (ppm) | Evaluation[1] (0–3 days[2]) | | (7–10 days) | |
|---|---|---|---|---|---|
| | | % Dead | % Feedings[3] | % Dead | % Feeding |
| I | 500 | 27 | 1 | 10 | 1 |
| | 100 | 13 | 9 | 7 | 7 |
| Untreated | — | 0 | 70 | 0 | 50 |

[1]Average of three replicates.
[2]Exposure started at 0 and 7 days after spraying and continued for 3 days.
[3]Percent of leaf consumed.

EXAMPLE 16

The foliage of Red Kidney bean plants (2 per pot) was sprayed to run-off with a solution of the hydrochloric acid salt of 3-dimethylamino-5-(4-methylpiperazin-1-yl)-1,2,4-dithiazolium chloride (I) at the concentrations indicated below. When the leaves had dried each plant was uniformly infested with ten 10-day-old Mexican bean beetle larvae. Results were evaluated after 4 days of exposure. Percent control was based on the number of larvae remaining on the plant. Percent feeding was based on the portion of the leaves consumed.

| Compound | Spray Concentration (ppm) | % Control | % Feeding |
|---|---|---|---|
| I | 500 | 100 | 12 |
| | 100 | 85 | 15 |
| Untreated Control | — | 0 | 90 |

EXAMPLE 17

The foliage of two Red Kidney beam plants was sprayed to run-off with a solution containing 10 ppm of the hydrochloric acid salt of 3-dimethylamino-5-(4-methylpiperazin-1-yl)-1,2,4-dithiazolium chloride. The following day the plants were infested with approximately 200 two-spotted mites (50 per leaf). No living mites could be found on these plants one week after treatment. Treated plants were growing vigorously and no phytotoxicity was observed. The leaves of untreated control plants were badly damaged by the existing mites and large numbers of eggs were present.

EXAMPLE 18

The foliage of tomato seedlings was sprayed to run-off with a 400 ppm solution of the hydrochloric acid salt of 3-dimethylamino-5-(4-methylpiperazin-1-yl)-1,2,4-dithiazolium chloride. The next day the seedlings were inoculated with a spore suspension of the late blight fungus Phytophthora infestans. They were then incubated in a saturated humidity chamber for one day. Similar inoculated seedlings which had not been treated with the chemicals of this invention were severely diseased after five days. Seedlings treated as above were almost completely free of disease and were rated as at least 80 percent control.

What is claimed is:

1. A method for protecting plants from mites, aphids, Colorado potato beetle, Mexican bean beetle, and boll weevil which comprises applying to the plant foliage a miticidally effective amount, an insecticidally effective amount or a plant protective amount, but less than a defoliating amount of at least one compound of the formula

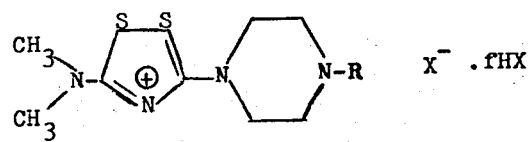

where
R is alkyl of 1 through 6 carbon atoms;
X$^-$ is an anion of the corresponding acid HX having an ionization constant of at least $1 \times 10^{-7}$; and $f$ is 0 or 1.

2. The method of claim 1 wherein R is alkyl of 1 through 4 carbon atoms.

3. The method of claim 1 wherein the compound applied is the hydrochloric acid salt of 3-dimethylamino-5-(4-methylpiperazin-1-yl)-1,2,4-dithiazolium chloride.

4. The method of claim 1 wherein the compound applied is the hydrobromic acid salt of 3-dimethylamino-5-(4-propylpiperazin-1-yl)-1,2,4-dithiazolium bromide.

5. The method of claim 1 wherein the compound is applied to a field crop at a rate in the range of about 0.01 to about 4 kg/ha.

6. The method of claim 1 wherein the compound is applied to a field crop at a rate in the range of about 0.01 to about 0.8 kg/ha.

7. The method of claim 1 wherein the compound is applied to trees by spraying the trees to run-off with a solution or suspension containing about 5 to about 4,000 ppm of the compound.

8. The method of claim 1 wherein the compound is applied to trees by spraying the trees to run-off with a solution or suspension containing about 10 to about 2,000 ppm of the compound.

9. The method of claim 1 wherein the compound is applied to trees by spraying the trees to run-off with a solution or suspension containing about 40 to about 500 ppm of the compound.

10. A method for controlling mosquitoes which comprises applying to the locus of mosquito larvae an insecticidally effective amount of at least one compound of the formula

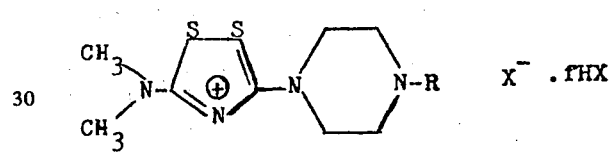

where
R is alkyl of 1 through 6 carbon atoms;
X$^-$ is an anion of the corresponding acid HX having an ionization constant of at least $1 \times 10^{-7}$; and $f$ is 0 or 1.

11. The method of claim 10 wherein R is alkyl of 1 through 4 carbon atoms.

12. The method of claim 10 wherein the compound applied is the hydrochloric acid salt of 3-dimethylamino-5-(4-methylpiperazin-1-yl)-1,2,4-dithiazolium chloride.

13. The method of claim 10 wherein the compound applied is the hydrobromic acid salt of 3-dimethylamino-5-(4-propylpiperazin-1-yl)-1,2,4-dithiazolium bromide.

* * * * *